United States Patent
Kleyer et al.

(10) Patent No.: US 9,556,327 B2
(45) Date of Patent: Jan. 31, 2017

(54) ADDITIVE FOR A SILICONE ENCAPSULANT

(71) Applicant: Dow Corning Corporation, Midland, MI (US)

(72) Inventors: Don L Kleyer, Hemlock, MI (US); Randall G Schmidt, Midland, MI (US); Adam C Tomasik, Mount Pleasant, MI (US); Shengqing Xu, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 14/906,579

(22) PCT Filed: Sep. 2, 2014

(86) PCT No.: PCT/US2014/053672
§ 371 (c)(1),
(2) Date: Jan. 21, 2016

(87) PCT Pub. No.: WO2015/034814
PCT Pub. Date: Mar. 12, 2015

(65) Prior Publication Data
US 2016/0177061 A1    Jun. 23, 2016

Related U.S. Application Data

(60) Provisional application No. 61/873,081, filed on Sep. 3, 2013.

(51) Int. Cl.
C08K 5/5419 (2006.01)
C07F 15/02 (2006.01)
H01L 23/29 (2006.01)

(52) U.S. Cl.
CPC ........... C08K 5/5419 (2013.01); C07F 15/025 (2013.01); H01L 23/296 (2013.01)

(58) Field of Classification Search
None
See application file for complete search history.

(56) References Cited

U.S. PATENT DOCUMENTS 3,377,312 A * 4/1968 Baney .................... C08L 83/04
524/262
2012/0065308 A1    3/2012 Sumi et al.

FOREIGN PATENT DOCUMENTS

EP          0231519 A2      8/1987
EP          0699717 A2      3/1996
WO      2013/052838 A1    4/2013

OTHER PUBLICATIONS

Kornev et al. "Ferrous tris(trimethylsilyl)silanolates: synthesis, structure, reactivity and thermal decomposition" Journal of Organometallic Chemistry 1999, 113-119.*

(Continued)

*Primary Examiner* — Robert S Loewe
(74) *Attorney, Agent, or Firm* — Timothy J. Troy; Claude F. Purchase

(57) ABSTRACT

An additive for a silicone encapsulant has the structure: Formula (I) wherein $R^1$ and $R^2$ are each $-O-Si(R^4)(R^5)(R^6)$ and each of $R^4$, $R^5$, and $R^6$ is independently chosen from $C_1-C_{10}$ hydrocarbyl groups, $C_1-C_{10}$ alkyl groups, $C_2-C_{10}$ alkenyl groups, and $C_6-C_{10}$ aryl groups, and wherein $R^3$ is independently chosen from $C_1-C_{10}$ hydrocarbyl groups, $C_1-C_{10}$ alkyl groups, $C_2-C_{10}$ alkenyl groups, and $C_6-C_{10}$ aryl groups. The additive is formed using a method that includes the step of reacting iron metal or an iron (III) compound with a hydroxyl functional organosiloxane. An encapsulant includes the additive and a polyorganosiloxane.

(Continued)

The encapsulant can be utilized to form a device that includes an electronic component and the encapsulant disposed on the electronic component. The device is formed using a method that includes the step of disposing the encapsulant on the electronic device.

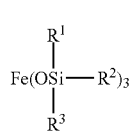

(I)

15 Claims, 2 Drawing Sheets

(56)     References Cited

OTHER PUBLICATIONS

PCT/US2014/053672 Search Report Dated Nov. 24, 2014.
Kleyer et al., U.S. Appl. No. 14/906,575, filed Jan. 21, 2016.
Yoshida et al., U.S. Appl. No. 14/769,131, filed Aug. 20, 2015.

\* cited by examiner

ADDITIVE FOR A SILICONE ENCAPSULANT

CROSS REFERENCE TO RELATED APPLICATIONS

This application is a U.S. national stage filing under 35 U.S.C. §371 of PCT Application No. PCT/US14/53672 filed on 2 Sep. 2014, which claims the benefit of U.S. Provisional Patent Application No. 61/873,081 filed 3 Sep. 2013 under 35 U.S.C. §119 (e). PCT Application No. PCT/US14/53672 and U.S. Provisional Patent Application No. 61/873,081 are hereby incorporated by reference.

FIELD OF THE DISCLOSURE

The present disclosure generally relates to an additive for a silicone encapsulant. More specifically, the additive has a particular structure, includes iron (III), and includes a series of ligands that include silicon, bonded to the iron.

DESCRIPTION OF THE RELATED ART

Silicone gels and encapsulants can be used to encapsulate electronic components and protect them from the environment. However, these encapsulants traditionally suffer from embrittlement, i.e., loss of ductility causing breakage or fragmentation, over time under stresses of high operating temperatures (e.g. >150° C.) or photo-energy flux, e.g. >1 W/cm$^2$) resulting in loss of protection and hence loss of performance within the device. As a result, additives have been added to silicone encapsulants in an attempt to mitigate these problems. Most are difficult to disperse uniformly within the silicone or result in opaque materials which limit the ability to inspect the electronic components without removing the encapsulant. Accordingly, there remains an opportunity to develop an improved additive for use in a silicone encapsulant.

SUMMARY OF THE DISCLOSURE

The present disclosure provides an additive for a silicone encapsulant and a method of forming the additive. The additive has the structure:

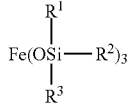

wherein R$^1$ and R$^2$ are each —O—SiR$^4$R$^5$R$^6$ and each of R$^4$, R$^5$, and R$^6$ is independently chosen from C$_1$-C$_{10}$ hydrocarbyl groups, C$_1$-C$_{10}$ alkyl groups, C$_2$-C$_{10}$ alkenyl groups, and C$_6$-C$_{10}$ aryl groups, and wherein R$^3$ is independently chosen from C$_1$-C$_{10}$ hydrocarbyl groups, C$_1$-C$_{10}$ alkyl groups, C$_2$-C$_{10}$ alkenyl groups, and C$_6$-C$_{10}$ aryl groups. The method includes the step of reacting iron metal or an iron (III) compound with a hydroxyl functional organosiloxane, e.g. in at least a 3:1 molar ratio when an iron (III) compound or iron metal is utilized.

This disclosure also provides an encapsulant that includes the additive and a polyorganosiloxane. The encapsulant can be utilized to form a device that includes an electronic component and the encapsulant disposed on the electronic component. The disclosure also provides a method of forming the device that includes the step of disposing the encapsulant on the electronic device.

BRIEF DESCRIPTION OF THE DRAWINGS

Other advantages of the present disclosure will be readily appreciated, as the same becomes better understood by reference to the following detailed description when considered in connection with the accompanying drawings wherein.

DETAILED DESCRIPTION OF THE DISCLOSURE

Figure 1:
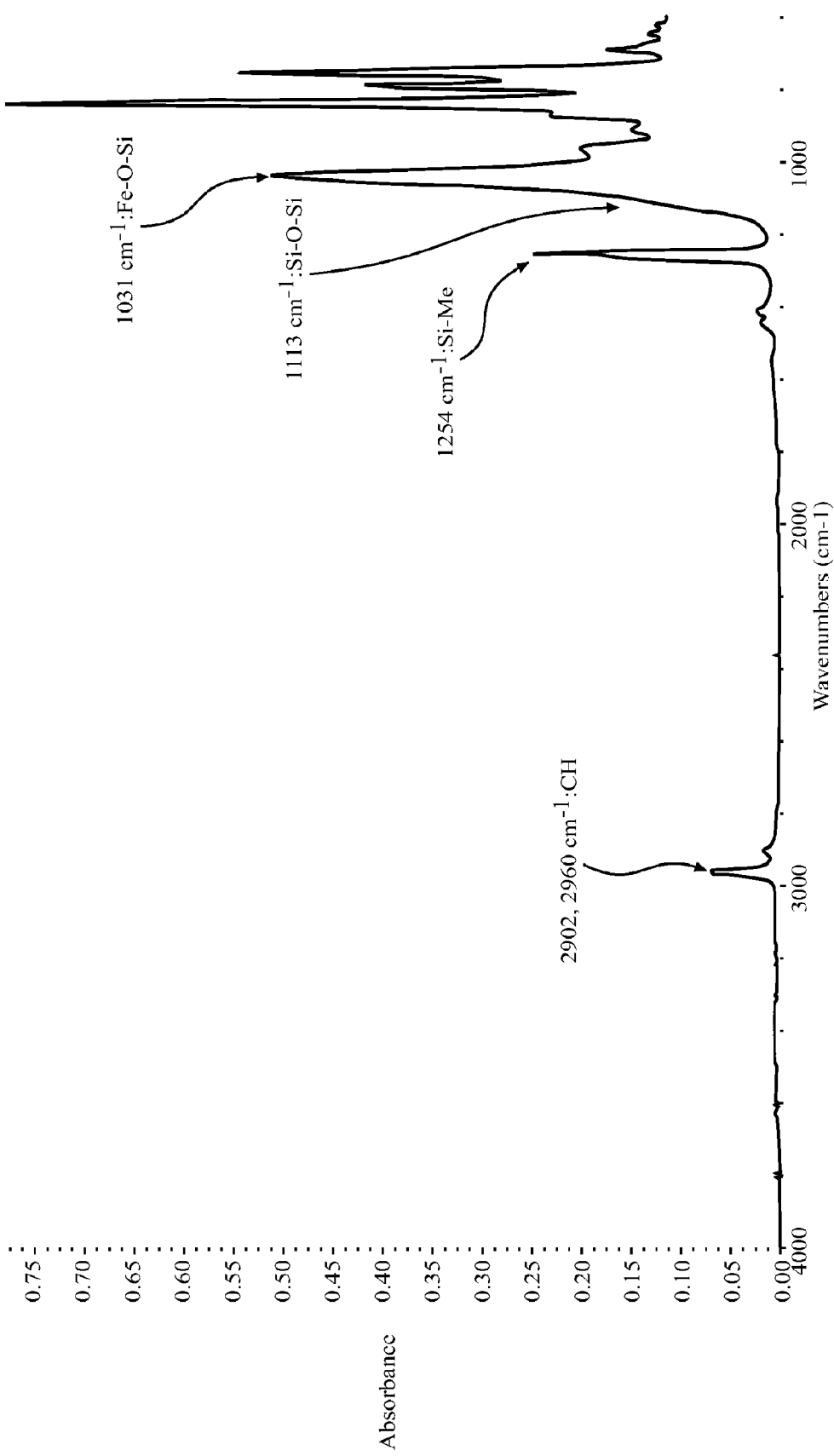
FIG. 1 is an ATR-FTIR spectrograph of Fe$^{Me}$, (Fe(OSiMe (OSiMe$_3$)$_2$)$_3$)

The present disclosure provides an additive for a silicone encapsulant. The additive has the structure:

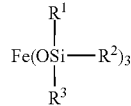

wherein the iron (Fe) is in a 3+ (III) oxidation state. In this 3+ state (III), the iron is typically bonded to three ligands. The aforementioned OSiR$^1$R$^2$R$^3$ structure may be alternatively described as a (monodentate) ligand, e.g. a trifunctional siloxy ligand, which may also be described as a tertiary silanol ligand or a trisubstituted silanol ligand.

In addition, in the aforementioned structure, R$^1$ and R$^2$ are each —O—Si(R$^4$)(R$^5$)(R$^6$). A non-limiting exemplary structure of the additive is set forth below. However, it is to be understood that any one or more of R$^4$, R$^5$, and/or R$^6$ may be in any location relative to the Si to which each is directly bonded.

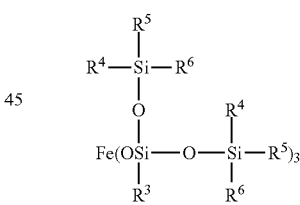

Each of R$^1$ and R$^2$ may be described as an "M" unit (e.g. R$_3$SiO$_{1/2}$ wherein R may be any one or more groups/moieties described herein), as is appreciated in the silicone arts, and each may be the same or may be different from one another. Each of R$^4$, R$^5$, and R$^6$ is independently chosen from C$_1$-C$_{10}$ hydrocarbyl groups, C$_1$-C$_{10}$ alkyl groups, C$_2$-C$_{10}$ alkenyl groups, and C$_6$-C$_{10}$ aryl groups. In addition, R$^3$ is independently chosen from C$_1$-C$_{10}$ hydrocarbyl groups, C$_1$-C$_{10}$ alkyl groups, C$_2$-C$_{10}$ alkenyl groups, and C$_6$-C$_{10}$ aryl groups. More specifically, each hydrocarbyl group may independently have 1, 2, 3, 4, 5, 6, 7, 8, 9, or 10 carbon atoms or any range of carbon atoms therebetween. Similarly, each alkyl group may independently have 1, 2, 3, 4, 5, 6, 7, 8, 9, or 10 carbon atoms, or any range of carbon atoms therebetween. In various embodiments, one or more alkyl groups is defined as a methyl group, ethyl group, propyl group, or butyl group. Each alkenyl group may independently have 2, 3, 4, 5, 6, 7, 8, 9, or 10 carbon atoms or any range of carbon atoms therebetween. In various embodiments, one or more alkenyl groups is defined as a vinyl group. Furthermore, each aryl group may independently have 6, 7, 8, 9, or 10 carbon atoms or any range of carbon atoms therebetween. In various embodiments, one or more aryl groups is further defined as a phenyl group.

In additional embodiments, at least 5, 10, 15, 20, 25, 30, 35, 40, 45, 50, 55, 60, 65, 70, 75, 80, 85, 90, 95, 96, 97, 98, or 99, mol percent of a total of the groups $R^3$-$R^6$ are methyl groups. In other embodiments, at least 5, 10, 15, 20, 25, 30, 35, 40, 45, 50, 55, 60, 65, 70, 75, 80, 85, 90, 95, 96, 97, 98, or 99, mol percent of a total of the groups $R^3$-$R^6$ are phenyl groups. It is contemplated that, in other embodiments, the aforementioned mol percent may describe each of $R^3$-$R^6$ considered individually and not as a whole. In still other embodiments, each of the groups $R^3$-$R^6$ may be a methyl group. Alternatively, each of the groups $R^3$-$R^6$ may be a phenyl group. Still further, in various embodiments, any three groups, e.g. each of $R^3$, $R^4$, and $R^6$, may be phenyl groups. In such embodiments, the structures may be as follows, or may be different:

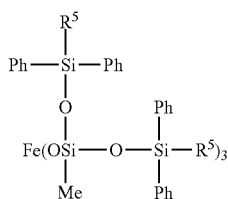

In an additional embodiment, the additive has the structure below (Structure (I)):

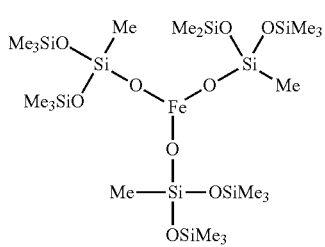

wherein Me is methyl. The aforementioned structure may be alternatively described as tris((1,1,1,3,5,5,5-heptamethyl-trisiloxan-3-yl)oxy)iron having the chemical formula $C_{21}H_{63}FeO_9Si_9$.

In another embodiment, the additive has the structure below (Structure (II)):

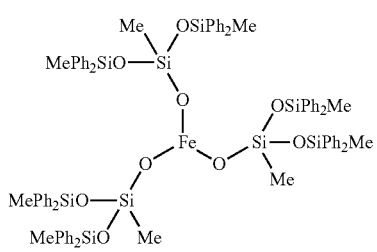

wherein Me is methyl and Ph is phenyl. The aforementioned structure may be alternatively described as tris((1,3,5-trimethyl-1,1,5,5-tetraphenyltrisiloxan-3-yl)oxy)iron having the chemical formula $C_{81}H_{87}FeO_9Si_9$. It is contemplated that additional embodiments may have the same chemical structure but different stereochemistry.

It is contemplated that the aforementioned structures may be simplified structures. For example, in one embodiment, the generic structure may be written as $[\text{Iron}(\text{OSiR}_3)_n]_x$ where x is the degree of molecular complexity. In one embodiment, the value of x does not matter because the empirical formula (or the ratio of Iron:Si) remains unchanged.

Physical Properties of the Additive:

The additive is not limited to having any particular physical properties so long as the structure is as described above. The additive may have a density of from 0.95 to 1.20, from 1.00 to 1.15, or from 1.05 to 1.10, g/cm$^3$, or any value or range of values therebetween. In addition, the additive may be described as being free of, or including less than 5, 4, 3, 2, 1, 0.5, 0.1, or 0.05 weight percent of, an alkaline earth metal salt or alkaline metal salt.

In other embodiments, the additive is soluble in an organofunctional silicone. The terminology "soluble in" typically describes that up to 50, 45, 40, 35, 30, 25, 20, 15, 10, 5, 4, 3, 2, or 1, grams of the additive may be soluble in 50, 55, 60, 65, 70, 75, 80, 85, 90, 95, 96, 97, 98, or 99 grams of the organofunctional silicone, respectively. Alternatively, the organofunctional silicone may be soluble in the additive. In such embodiments, for example, the terminology "soluble in" typically describes that up to 50, 45, 40, 35, 30, 25, 20, 15, 10, 5, 4, 3, 2, or 1, grams of the organofunctional silicone may be soluble in 50, 55, 60, 65, 70, 75, 80, 85, 90, 95, 96, 97, 98, or 99 grams of the additive, respectively. Typically, a determination of "solubility" is determined visually when the additive and the organofunctional silicone are combined as no phase separation is seen by the naked eye. However, solubility may alternatively be assessed by one or more standardized (e.g. ASTM) tests, as appreciated in the silicone arts.

For example, the additive may be deemed to be soluble in the organofunctional silicone or vice versa, when, the combination consisting of the two, i.e., the additive and the organofunctional siloxane, shows no visible signs of non-homogeneity (e.g. settling or non-uniform phase separation) after 24 hours at room temperature. The organofunctional silicone described above may be the same as the polyorganosiloxane that will be described in greater detail below, may be a silicone fluid, e.g. Dow Corning 200 fluid, polydimethylsiloxane, or a phenyl substituted siloxane such as Dow Corning 510 fluid.

In additional embodiments, the additive includes 1 to 20, 5 to 20, 6 to 20, 10 to 20, 15 to 20, 5 to 10, 10 to 15, 5 to 15, 3 to 25, 1, 2, 3, 4, 5, 6, 7, 8, 9, 10, 11, 12, 13, 14, 15, 16, 17, 18, 19, 20, 21, 22, 23, 24, or 25, weight percent of iron based on a total weight of the additive, or any value or range of values therebetween. The weight percent of iron is typically determined by the chemical structure of the additive itself. For example, Structure (I) above includes about 7.11-7.27% weight percent of iron. Structure (II) above includes about 2.92-3.69% weight percent of iron.

In other embodiments, the additive may be alternatively described as a cluster, e.g. an iron silyloxide cluster. For example, individual molecules of the additive, having the general structure described above, may cluster together via covalent bonds or intermolecular forces. For example, the additive may cluster into groups of 2, 3, 4, 5, 6, 7, 8, 9, or 10, or even more, units or individual additive molecules. Non-limiting examples of these clusters may have the following formula wherein n is a number as set forth immediately above or any range of numbers therebetween:

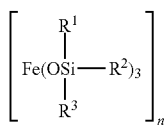

It is also contemplated that the additive could be complexed with a neutral donor ligand via a dative interaction. In some embodiments the additive is further complexed with the neutral donor ligand, and in other embodiments is not complexed with and lacks the neutral donor ligand. Examples of neutral donor ligands can include but are not limited to, amines (e.g. pyridine, triethylamine, $NH_3$), ethers (e.g. tetrahydrofuran, dioxane, diethylether), alkenes/alkynes (e.g. ethylene, acetylene), aromatics (e.g. benzene, toluene), alcohols (e.g. ethanol, phenol), silanols (e.g. excess $HOSi(R^1)(R^2)(R^3)$, trimethylsilanol), phosphines (e.g. tricyclohexylphosine, triphenylphosphine), thiols (e.g. decylmercaptan), etc. It is also contemplated that more than one of these species may be simultaneously present in the interaction or in any combination from the non-limiting list of donor ligands. Typically these ligands include a heteroatom such as N, O, P, S, or As, Se, Te, B, etc. These types of ligands can be used to break up the aforementioned clusters. In addition, it is contemplated that the additive may include one or more bidentate and/or tridentate ligands that contain one or multiple silanol attachment points to the exclusion of the monodentate ligands described above, e.g. so long as the $M-O-Si(R^1)(R^2)(R^3)$ ligand is present. If there are multiple attachment points on the ligand, a high molecular weight cluster may be formed.

Reaction Products:

In one embodiment, the additive is described as a reaction product of a reaction of an iron alkoxide and a hydroxyl functional organosiloxane. Said differently, in this embodiment, the additive results from, or is the product of, the reaction of the iron alkoxide and the hydroxyl functional organosiloxane. The iron alkoxide is not particularly limited. In various embodiments, the iron alkoxide is further defined as $Fe(O-R)_3$, corresponding to iron (III), as is appreciated in the art. Each R ($R^4$, $R^5$, $R^6$) may be independently chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups. These hydrocarbyl, alkyl, alkenyl, and aryl groups, and the corresponding numbers of carbon atoms therein, may be as described above. This reaction may proceed as set forth below:

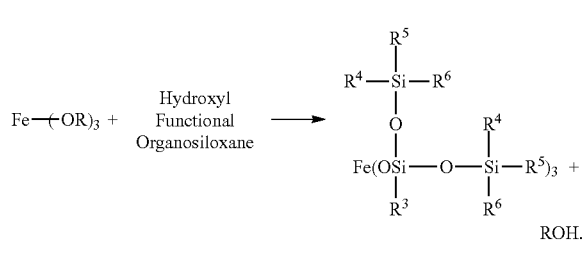

Hydroxyl Functional Organosiloxane:

The hydroxyl functional organosiloxane as described above is not particularly limited. In one embodiment, the hydroxyl functional organosiloxane has the formula $M^1D^{R,OH}M^2$. In this formula, R may be any group described above or below. Also in this embodiment, the nomenclature "M" and "D" represent an "M unit" and a "D" unit (e.g. $R_2SiO_{2/2}$ wherein R may be any one or more groups/moieties described herein), respectively, as appreciated in the silicone arts. Similarly, the nomenclature R,OH describes that the silicon atom of the D unit is bonded to an R group and also to an OH group. In one embodiment, each of $M^1$ and $M^2$ independently have the formula $O-Si(R^4)(R^5)(R^6)$, wherein $R^4$, $R^5$, and $R^6$ are as described above. $M^1$ and $M^2$ may be the same or may be different. In various embodiments, the hydroxyl functional organosiloxane has one or more of the structures:

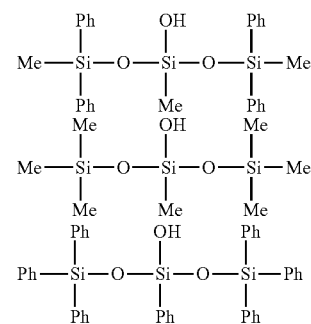

wherein Me is methyl and Ph is phenyl. It is contemplated that a single hydroxyl functional organosiloxane, or two or more hydroxyl functional organosiloxanes may be utilized.

The hydroxyl functional organosiloxane may be formed by any method known in the art. For example, the hydroxyl functional organosiloxane may be formed by a method that includes one or more steps as described immediately below:

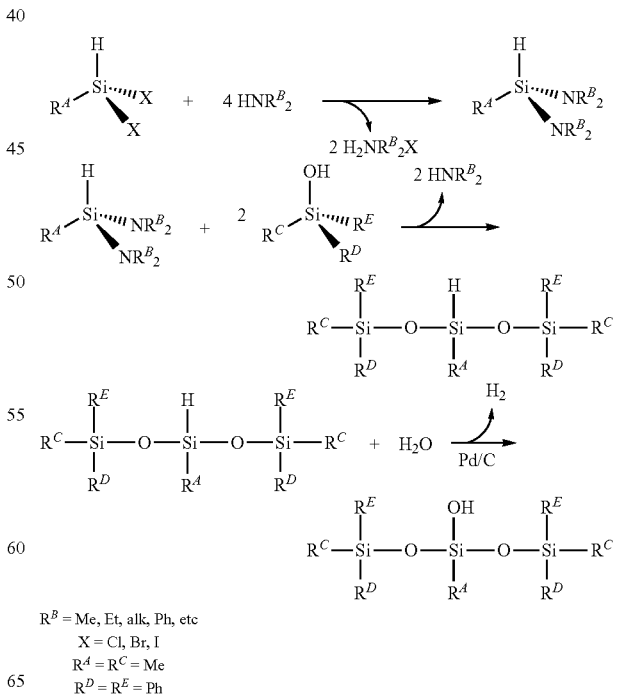

$R^B$ = Me, Et, alk, Ph, etc
X = Cl, Br, I
$R^A$ = $R^C$ = Me
$R^D$ = $R^E$ = Ph Method of Making the Additive:

This disclosure also provides a method of making the additive. The additive may be formed by any method in the art. Similarly, the method may include any of the reactions described above. Typically, the additive is formed such that no (or less than 5, 4, 3, 2, 1, 0.5, 0.1, or 0.05 weight percent of an alkaline earth metal salt or alkaline metal salt) is formed in the process. In other words, the additive is typically free of, or includes less than 5, 4, 3, 2, 1, 0.5, 0.1, or 0.05 weight percent of an alkaline earth metal salt or alkaline metal salt.

In one embodiment, the method includes the step of reacting iron metal or an iron (III) compound with the hydroxyl functional organosiloxane, e.g. in at least a 3:1 molar ratio when an iron (III) compound or iron metal is utilized. Alternatively, a molar excess of the hydroxyl functional organosiloxane may be utilized. Just as above, the iron (III) compound may be any of the compounds described above.

In one embodiment, the method produces an alcohol and the method further comprises the step of separating the alcohol from the additive. Typically, the alcohol (represented above as ROH) may be any known in the art. However, the alcohol typically includes an R group from the iron alkoxide. The alcohol may be removed from the additive by any means known in the art, including distillation. Alternatively, this step may be described as removing the additive from the alcohol, e.g. depending on temperature of distillation. It is contemplated that the alcohol may not be removed.

In other embodiments, iron (III) additives can be formed by one or more of the following reactions/equations:

$FeX_3 + 3(Alkaline/Alkaline\ Earth)OSiR_3 \rightarrow Fe(OSiR_3)_3 + 3(Alkaline/Alkaline\ Earth)X$

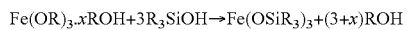
$Fe(OR)_3 \cdot xROH + 3R_3SiOH \rightarrow Fe(OSiR_3)_3 + (3+x)ROH$

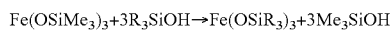
$Fe(OSiMe_3)_3 + 3R_3SiOH \rightarrow Fe(OSiR_3)_3 + 3Me_3SiOH$

$Fe + 3R_3SiOH \rightarrow Fe(OSiR_3)_3 + 1.5H_2$ wherein X is Cl, Br, or I, R is any group described above, and the terminology "Alkaline/Alkaline Earth" describes an alkaline or alkaline earth metal such as Na/K, Rb or Mg/Ca/Sr, respectively. Typically, Na or K is utilized.

Silicone Encapsulant:

This disclosure also provides a silicone encapsulant. The silicone encapsulant may alternatively be described as a silicone gel. Alternatively, the silicone encapsulant can be alternatively described as a polyorganosiloxane encapsulant wherein the terminology "silicone" includes or is a polymeric or oligomeric siloxane. The terminology "silicone" may be used interchangeably with polyorganosiloxane or may describe a specific compound, such as a silicone rubber, e.g. that may or may not be curable. The silicone encapsulant includes the additive and also a silicone, a polyorganosiloxane, or a polyorganosiloxane composition that itself includes one or more silicones or polyorganosiloxanes. The additive and the silicone, polyorganosiloxane, or a polyorganosiloxane composition that itself includes one or more silicones or polyorganosiloxanes, may be present in a combination, mixture, or admixture.

Typically, the additive is present in the encapsulant in an amount such that the iron is present in an amount of from 5 to 1000 parts by weight per one million parts by weight (ppm) of the encapsulant. In various embodiments, the additive is present in amounts such that the iron is present in an amount from 5 to 995, from 10 to 90, 15 to 985, 20 to 980, 25 to 975, 30 to 970, 35 to 965, 40 to 960, 45 to 955, 50 to 950, 55 to 945, 60 to 940, 65 to 935, 70 to 930, 75 to 925, 80 to 920, 85 to 915, 90 to 910, 95 to 905, 100 to 900, 105 to 895, 110 to 890, 115 to 885, 120 to 880, 125 to 875, 130 to 870, 135 to 865, 140 to 860, 145 to 855, 150 to 850, 155 to 845, 160 to 840, 165 to 835, 170 to 830, 175 to 825, 180 to 820, 185 to 815, 190 to 810, 195 to 805, 200 to 800, 205 to 795, 210 to 790, 215 to 785, 220 to 780, 225 to 775, 230 to 770, 235 to 765, 240 to 760, 245 to 755, 250 to 750, 255 to 745, 260 to 740, 265 to 735, 270 to 730, 275 to 725, 280 to 720, 285 to 715, 290 to 710, 295 to 705, 300 to 700, 305 to 695, 310 to 690, 315 to 685, 320 to 680, 325 to 675, 330 to 670, 335 to 665, 340 to 660, 345 to 655, 350 to 650, 355 to 645, 360 to 640, 365 to 635, 370 to 630, 375 to 625, 380 to 620, 385 to 615, 390 to 610, 395 to 605, 400 to 600, 405 to 595, 410 to 590, 415 to 585, 420 to 580, 425 to 575, 430 to 570, 435 to 565, 440 to 560, 445 to 555, 450 to 550, 455 to 545, 460 to 540, 465 to 535, 470 to 530, 475 to 525, 480 to 520, 485 to 515, 490 to 510, or 495 to 505, parts by weight per one million parts by weight (ppm) of the encapsulant. It is contemplated that, in additional embodiments, the additive may be present in the encapsulant such that the iron is present in any amount or range of amounts therebetween any value(s) set forth above.

The silicone encapsulant is not particularly limited relative to physical properties. In various embodiments, the silicone encapsulant has a) a translucent to optically clear appearance, b) some flexibility characterized by an elongation to break ≥30%, and/or c) a modulus consistent with elastomeric character (as appreciated in the art) between 0.1 and 100 MPa. In other embodiments, the silicone encapsulant is opaque ((e.g. when utilized in/as a remote phosphor or a die attach).

Polyorganosiloxane (Composition):

The polyorganosiloxane first introduced above as utilized in the encapsulant is not particularly limited and may be any in the art. In one embodiment, the polyorganosiloxane is curable. In another embodiment, the polyorganosiloxane is cured, e.g. prior to, concurrently with, or after, addition of the additive. In still other embodiments, the polyorganosiloxane is not curable and may be, for example, a silicone fluid such as PDMS.

In various embodiments, the polyorganosiloxane has a viscosity of from greater than zero to less than 500,000, 450,000, 400,000, 350,000, 300,000, 250,000, 200,000, 150,000, 100,000, 50,000, 25,000, 20,000, 15,000, 10,000, or 5,000, centistokes measured at 25° C. In other embodiments, the polyorganosiloxane has a viscosity of from 5,000 to 50,000, from 10,000 to 45,000, from 15,000 to 40,000, from 20,000 to 35,000, from 25,000 to 30,000, centistokes measured at 25° C. Alternatively, the polyorganosiloxane may have a viscosity of any value or range of values between any of the aforementioned values.

Curable Polyorganosiloxane (Composition):

As described above, the polyorganosiloxane (composition) may be curable. Examples of curable polyorganosiloxanes (and compositions) include, but are not limited to, hydrosilylation-curable polyorganosiloxanes, condensation-curable polyorganosiloxanes, radiation-curable polyorganosiloxanes, and peroxide-curable polyorganosiloxanes.

In one embodiment, the polyorganosiloxane (composition) is hydrosilylation curable or condensation curable. In another embodiment, the polyorganosiloxane (composition) is hydrosilylation curable. In still another embodiment, the polyorganosiloxane (composition) is condensation curable. The polyorganosiloxane (composition) can be cured by exposure to ambient temperature, elevated temperature, moisture, or radiation, depending on the type of polyorganosiloxane(s) present.

A hydrosilylation-curable polyorganosiloxane composition typically includes a polyorganosiloxane that has an average of at least two silicon-bonded alkenyl groups or silicon-bonded hydrogen atoms per molecule. This composition also typically includes an organosilicon compound in an amount sufficient to cure the polyorganosiloxane composition, wherein the organosilicon compound typically has an average of at least two silicon-bonded hydrogen atoms or silicon-bonded alkenyl groups per molecule capable of reacting with the silicon-bonded alkenyl groups or silicon-bonded hydrogen atoms of the polyorganosiloxane. The composition may also include a catalytic amount of a hydrosilylation catalyst. Typically, this type of polyorganosiloxane composition can be cured by exposure to a temperature of from room temperature (~23±2° C.) to 250° C., alternatively from room temperature to 150° C., alternatively from room temperature to 115° C., at atmospheric pressure. The polyorganosiloxane composition is generally heated for a length of time sufficient to cure (cross-link) the polyorganosiloxane.

A condensation-curable polyorganosiloxane composition typically includes a polyorganosiloxane having an average of at least two silicon-bonded hydrogen atoms, hydroxy groups, or hydrolysable groups per molecule and, optionally, a cross-linking agent having silicon-bonded hydrolysable groups and/or a condensation catalyst. Typically, this type of composition cures depending on the nature of the silicon-bonded groups of the polyorganosiloxane. For example, when a polyorganosiloxane includes silicon-bonded hydroxy groups, the composition can be cured (i.e., cross-linked) by heating. The composition can typically be cured by heating at a temperature of from 50 to 250° C., for a period of from 1 to 50 h. When the condensation-curable polyorganosiloxane includes a condensation catalyst, the composition can typically be cured at a lower temperature, e.g., from room temperature (~23±2° C.) to 150° C.

Alternatively, condensation-curable polyorganosiloxane compositions that include a polyorganosiloxane having silicon-bonded hydrogen atoms can be cured by exposing the composition to moisture or oxygen at a temperature of from 100 to 450° C. for a period of from 0.1 to 20 h. When the condensation-curable polyorganosiloxane includes a condensation catalyst, the composition can typically be cured at a lower temperature, e.g., from room temperature (~23±2° C.) to 400° C. Further, condensation-curable polyorganosiloxane composition that include a polyorganosiloxane having silicon-bonded hydrolysable groups can be cured by exposing the composition to moisture at a temperature of from room temperature (~23±2° C.) to 250° C., alternatively from 100 to 200° C., for a period of from 1 to 100 h. For example, the polyorganosiloxane can typically be cured by exposing it to a relative humidity of 30% at a temperature of from about room temperature (~23±2° C.) to 150° C., for a period of from 0.5 to 72 h. Cure can be accelerated by application of heat, exposure to high humidity, and/or addition of a condensation catalyst to the composition.

A peroxide-curable polyorganosiloxane composition typically includes a polyorganosiloxane having silicon-bonded unsaturated aliphatic hydrocarbon groups and an organic peroxide. Such a composition can typically be cured by exposure to a temperature of from room temperature (~23±2° C.) to 180° C., for a period of from 0.05 to 1 h.

A radiation-curable polyorganosiloxane composition typically includes a polyorganosiloxane having an average of at least two silicon-bonded radiation-sensitive groups per molecule and, optionally, a cationic or free-radical photoinitiator depending on the nature of the radiation-sensitive groups in the polyorganosiloxane. Such a composition can typically be cured by exposing the composition to an electron beam and/or ultraviolet radiation. Typically, the accelerating voltage is from about 0.1 to 100 keV, the vacuum is from about 10 to 10-3 Pa, the electron current is from about 0.0001 to 1 ampere, and the power varies from about 0.1 watt to 1 kilowatt. The dose is typically from about 100 microcoulomb/cm$^2$ to 100 coulomb/cm$^2$, alternatively from about 1 to 10 coulombs/cm$^2$. Depending on the voltage, the time of exposure is typically from about 10 seconds to 1 hour. Also, if such a composition includes a cationic or free radical photoinitiator, the composition can typically be cured by exposing it to radiation having a wavelength of from 150 to 800 nm, alternatively from 200 to 400 nm, at a dosage sufficient to cure. The light source is typically a medium pressure mercury-arc lamp. The dose of radiation is typically from 30 to 1,000 mJ/cm$^2$, alternatively from 50 to 500 mJ/cm$^2$. Moreover, the polyorganosiloxane can be externally heated during or after exposure to radiation to enhance the rate and/or extent of cure.

Cured Polyorganosiloxane (Composition):

The aforementioned cured polyorganosiloxane (composition) may be alternatively described as the cured product of any one or more of the aforementioned curable compositions. Typically, the additive is added to a cured composition prior to curing. However, it is contemplated that the additive may be added to a cured composition after that composition has been cured. For example, the additive may be physically mixed or blended with the composition after the composition has been cured.

Non-Curable Polyorganosiloxane (Composition):

The aforementioned non-curable polyorganosiloxane (composition) may be alternatively described as a silicone fluid that is non-reactive. A typical silicone fluid is PDMS. In various embodiments, the silicone fluid has a viscosity at 25° C. of from about 0.001 to about 50 Pa·s, typically from about 0.02 to about 10 Pa·s, and more typically from about 0.05 to about 5 Pa·s. The silicone fluid can be linear, branched, cyclic, or a mixture thereof. Mixtures of the aforementioned fluids may also be used. Many of the linear, branched, and cyclic silicone fluids have melting points below about 25° C. Such materials are also commonly described as silicone liquids, silicone fluids, or silicone oils. A detailed description of non-limiting silicone fluids can be found in many references, including "Chemistry and Technology of Silicones" by W. Knoll, Academic Press, 1968, which, in one embodiment, is incorporated herein by reference relative to the silicone fluids.

Non-limiting examples of linear silicone fluids suitable for use herein include trimethylsiloxy-terminated dimethylsiloxane fluids sold by Dow Corning Corporation under the trade name "Dow Corning® 200 Fluids". These silicone fluids are manufactured to yield essentially linear oligomers and/or polymers typically having a viscosity of from 0.001 to about 50 Pa·s at 25° C. Such fluids are primarily linear but can include cyclic and/or branched structures. In one embodiment, the silicone fluid is a trimethylsiloxy-terminated polydimethylsiloxane having a viscosity of about 0.1 Pa·s at 25° C.

Additional non-limiting examples of suitable cyclic silicone fluids include the cyclic polydimethylsiloxanes sold by Dow Corning Corporation under the trade names "Dow Corning® 244, 245, 344, and 345 Fluids", depending on the relative proportions of octamethylcyclotetrasiloxane and decamethylcyclopentasiloxane. Mixtures of the straight-chain and cyclic dimethyl may also be utilized. Even additional non-limiting examples of suitable silicone fluids are $Me_3SiO[(OSiMe_3)_2SiO]SiMe_3$ and $Me_3SiO[(OSiMe_3)MeSiO]SiMe_3$.

Additional Components:

The encapsulant and/or any of the aforementioned polyorganosiloxane (compositions) may include one or more additional components such as catalysts, fillers, other reactants, light activated compounds such as phosphors or quantum dots, etc.

Device:

This disclosure also provides a device. The device may be used for various applications. In various embodiments, the device is or includes a power modules based on Si substrates or wide band gap semiconductor substrates that operate at ever-increasing temperatures. For example, the power module can be used for power inversion. In other embodiments, the device includes a dielectric gel, potant, or overmold. For example, the device may include an electronic component and an encapsulant, e.g. as a gel, including the additive, disposed on the electronic component as protection, e.g. as a dielectric, physical, or gas/liquid barrier.

In various embodiments, the additive is utilized in a composition, such as a silicone encapsulant, that is used to protect power modules and other electronic components from the environment when used in high operating temperature devices at temperatures >150° C., >180° C., >200° C., >225° C., and up to 250° C., 300° C., 350° C., or 400° C.

The device may be or include the electronic component and the encapsulant, including the additive, disposed on the electronic component. The electronic component is not particularly limited and may be further defined as an electronic semiconductor. Alternatively, the electronic component may be further defined as a component that sources and/or detects and controls light such as visible light, gamma rays, x-rays, ultraviolet rays, and infrared rays. In various embodiments, the electronic component is a photovoltaic (solar) cell or (light emitting) diodes. In still other embodiments, the electronic component is further defined as an optoelectronic component.

Electronic semiconductors typically operate as electrical-to-optical or optical-to-electrical transducers. Typical, but non-limiting electronic semiconductors include photodiodes including solar cells, phototransistors, photomultipliers, integrated optical circuit (IOC) elements, photoresistors, photoconductive camera tubes, charge-coupled imaging devices, injection laser diodes, quantum cascade lasers, light-emitting diodes, photoemissive camera tubes, and the like. In one embodiment, the electronic semiconductor is further defined as a solar cell. In another embodiment, the electronic semiconductor is further defined as a light emitting diode.

The electronic semiconductor is not particularly limited and may be any known in the art. Typically, the electronic semiconductor has an electrical conductivity of from about $10^3$ S/cm to about $10^{-8}$ S/cm. In one embodiment, the electronic semiconductor includes silicon. In other embodiments, the electronic semiconductor includes arsenic, selenium, tellurium, germanium, gallium arsenide, silicon carbide, and/or elements from Groups IV, III-V, II-VI, I-VII, IV-VI, V-VI, and II-V, and may be of p- or n-type. It is contemplated that the electronic semiconductor (12) may be disposed on a substrate, such as glass, using chemical vapor deposition (CVD).

The electronic semiconductor has a first side and a second side. Typically the first side is opposite the second side. However, the first and second sides may be adjacent each other. In various embodiments, one or more of electrical leads are attached to one or both of the first and second sides to connect a series of electronic semiconductors together. The electrical leads may be of any size and shape and typically are rectangular-shaped. In one embodiment, the electrical leads have dimensions of approximately 0.005 to 0.080 inches in length and/or width. In other embodiments, the electrical leads have a thickness of from 0.005 to 0.015, from 0.005 to 0.010, or from 0.007 to 0.010, inches. The electrical leads may be of any type known in the art and may be disposed on any portion of the electronic semiconductor.

Typically, one electrical lead acts as an anode while another electrical lead acts as a cathode. In various embodiments, the electronic semiconductor includes one or more electrical leads disposed thereon, e.g. first, second, third, and fourth electrical leads. These electrical leads may be the same or may be different from each other (i.e., made from the same material or from different materials) and may include metals, conducting polymers, and combinations thereof. In one embodiment, the one or more electrical leads include tin-silver solder coated copper. In another embodiment, the one or more electrical leads include tin-lead solder coated copper. The electronic semiconductor itself is not limited in size or shape and may be any size or shape known in the art.

Substrate/Superstrate:

The device may also include a substrate and/or a superstrate. Typically, the substrate provides protection to a rear surface of the device while a superstrate typically provides protection to a front surface of the device. The substrate and the superstrate may be the same or may be different and each may independently include any suitable material known in the art. The substrate and/or superstrate may be soft and flexible or may be rigid and stiff. Alternatively, the substrate and/or superstrate may include rigid and stiff segments while simultaneously including soft and flexible segments. The substrate and/or superstrate may be transparent to light, may be opaque, or may not transmit light (i.e., may be impervious to light). Typically, the superstrate transmits light. In one embodiment, the substrate and/or superstrate includes glass. In another embodiment, the substrate and/or superstrate includes metal foils, polyimides, ethylene-vinyl acetate copolymers, and/or organic fluoropolymers including, but not limited to, ethylene tetrafluoroethylene (ETFE), Tedlar®, polyester/Tedlar®, Tedlar®/polyester/Tedlar®, polyethylene terephthalate (PET) alone or coated with silicon and oxygenated materials ($SiO_X$), and combinations thereof. In one embodiment, the substrate is further defined as a $PET/SiO_x$-PET/Al substrate, wherein x has a value of from 1 to 4.

The substrate and/or superstrate may be load bearing or non-load bearing and may be included in any portion of the device. Typically, the substrate is load bearing. The substrate may be a "bottom layer" of the device that is typically positioned behind the electronic semiconductor and serves as mechanical support. Alternatively, the device may include a second or additional substrate and/or superstrate. The substrate may be the bottom layer of the device while a second substrate may be the top layer and function as the superstrate. Typically, the second substrate (e.g. a second substrate functioning as a superstrate is transparent to the solar spectrum (e.g. visible light) and is positioned on top of the substrate. The second substrate may be positioned in front of a light source. The second substrate may be used to protect the device from environmental conditions such as rain, show, and heat. Most typically, the second substrate functions as a superstrate and is a rigid glass panel that is transparent to sunlight and is used to protect the front surface of the device.

The substrate and/or superstrate typically have a thickness of from 50 to 500, of from 100 to 225, or of from 175 to 225, micrometers. The substrate and/or superstrate may have a length and width of 125 mm each or a length and width of 156 mm each. of course, the invention is not limited to these thicknesses or ranges thereof and the thickness of the substrate and/or superstrate may be any value or range of values, both whole and fractional, within those ranges and values described above or different therefrom. It is also contemplated that the thickness, length, and/or width of the substrate and/or superstrate may vary from the values and/or range of values above by ±5%, ±10%, ±15%, ±20%, ±25%, ±30%, etc.

In certain embodiments, the device is used for solid-state lighting (SSL) applications. For example, one or more of the devices may be used for general lighting applications, such as for lighting residential, commercial, and/or industrial spaces. Such lighting may be direct lighting, indirect lighting, or a combination thereof. The device can be used separately or in an array. The device may be used for other applications as well, such as for automotive applications, display applications, backlighting applications, etc. The device may be of various constructs. For example, the device may be configured as a light bulb, a luminaire, a light engine, or a lamp. The device may be configured into any type of construct. In still other embodiments, the device may be or include a remote phosphor binder, a secondary optic and/or light guide, a white reflector, a phosphor conversion layer binder, or a die attach adhesive film. In other embodiments, the device may be or include a light guide panel, light guide sheet, light guide film, etc. or a wave guide.

Referring back, the device also includes the encapsulant that is disposed on the electronic component. The terminology "disposed on" includes the encapsulant disposed on and in direct contact with the electronic device. This terminology also includes the encapsulant spaced apart from the electronic device yet still disposed thereon. The encapsulant may be disposed on the electronic device such that only one side of the electronic device is covered. Alternatively, the encapsulant may partially or entirely encapsulate the electronic device or any other component described herein. In various embodiments, the encapsulant is a sheet, gel, film, paste, or liquid. Most typically, the encapsulant is a sheet or a film. It is contemplated that, in various embodiments, the additive and the silicone encapsulant may be used to form one part of a device or the entire device itself.

Additional Components:

In certain embodiments, the device further comprises a light transmissive cover disposed over the luminescent layer and/or encapsulant, e.g. opposite the light emitting diode. If utilized, the light transmissive cover is typically spaced from the luminescent layer and/or encapsulant. The light transmissive cover may be formed from various materials and may be formed from a material that is the same as or different from the material of the host material of the luminescent layer and/or encapsulant. In certain embodiments, the light transmissive cover is formed from a glass, an epoxy, or a polycarbonate. The light transmissive cover is useful for protecting the luminescent layer, the encapsulant, and/or the light emitting diode.

In various embodiments, the device further comprises at least one reflector, e.g. disposed adjacent the light emitting diode. The reflector is typically spaced from at least a portion of the luminescent layer and/or encapsulant. The reflector can be of various shapes, and typically has a dish, parabolic, or frustoconical shape. The light emitting diode is typically disposed in the middle of the reflector. However, the light emitting diode may also be offset from center. The reflector can be formed from various materials, such as a metal. Various types of metals can be used to form the reflector and other materials may be used as well provided they provide a degree of reflection. The reflector may be useful for directing light emitted by the light emitting diode and, optionally, the luminescent layer and/or encapsulant, outwardly away from the device.

In further embodiments, the device can comprise any number of other additional components generally associated with conventional light emitting devices. For example, the device can include one or more wire bonds, a submount, and/or a heat sink. As further examples, the device can comprise a circuit board and/or a lens. If utilized, the circuit board can be programmed to include lighting controls such as dimming, light sensing and pre-set timing. Such controls are especially useful for packages.

Method of Making the Device:

This disclosure also provides a method of making the device. The method includes the step of disposing the silicone encapsulant on the electronic component. In one embodiment, the step of disposing is further defined as disposing the silicone encapsulant on and in direct contact with the electronic component. In another embodiment, the step of disposing is further defined as disposing the silicone encapsulant on and apart from the electronic component.

The encapsulant and/or any one or more compositions or components described above may be deposited by any means known in the art including using a brush/trowel, spraying, pouring, dipping, utilizing a dispensing nozzle, roll coating, transfer printing, screen printing, curtain coating, or any method known in the art. It is contemplated that the step of depositing may be alternatively described as dispensing, disposing, applying, or coating. In one embodiment, the method may include first dispensing, e.g. through one or more spray nozzles, followed by manual troweling and optionally a combination of dispensing a mass followed by automated troweling. For example, this may be possible when utilizing long pot life compositions.

The method may also include the step of laminating any one or more of the aforementioned components or layers. The step of laminating is not particularly limited and may include any one or more laminating techniques known in the art. For example, the step of laminating may be described as contacting and/or compressing any one or more of the above with another. The step of compressing may include applying a mechanical weight, press, or roller (e.g. a pinch roller). The step of compressing may be further defined as applying a force on the interior (e.g. at the center) of the device or any one or more layers of components. This force may be moved towards the perimeter or edges of the device. For example, this force may be applied at the center and then moved outwards to assist in the evacuation of air from the device.

The step of laminating or, for example compressing, may also include the step of applying a vacuum to one or more of the aforementioned components. Alternatively, the step of applying a vacuum may be performed independent of the step of laminating or compressing or may not be utilized at all. Still further, the step of laminating may include the step of applying heat to one or more of the aforementioned components. Alternatively, the step of applying heat may be independent from the step of laminating or compressing or not be utilized at all.

EXAMPLES

A first series of examples that include the encapsulant and the additive are formed. These Examples include a PDMS test matrix as the encapsulant that is formed from a mixture of Dimethylvinylsiloxy-terminated Dimethyl Siloxane and Trimethylsiloxy-terminated Dimethyl, Methylhydrogen siloxane that are reacted at an SiH:Vinyl ratio of 1.0 in the presence of 5 ppm of Pt complexed with dimethylvinylsiloxy terminated PDMS. These examples include varying amounts (5-2000 ppm) of iron in one or more additives. A comparative example is also formed and is identical to the aforementioned but does not include any additive.

A second series of examples includes a phenyl test matrix as the encapsulant formed from a mixture of Dimethylvinylsiloxy-terminated methylphenylsiloxane, Tetramethyltetravinylcyclotetrasiloxane, Phenylsilsesquioxane, dimethylhydrogen-terminated, and Dimethylhydrogen-terminated diphenylsiloxane that are reacted at an SiH:Vinyl ratio of 1.0 in the presence of 2.5 ppm of Pt complexed to dimethylvinylsiloxy-terminated methylphenylsiloxane. These examples include varying amounts (5-2000 ppm) of iron in one or more additives. A second comparative sample is also formed and is identical to the immediately aforementioned second series of examples but does not include any additive.

To form the examples, the components (and optionally the additives) are mixed and cast and press cured as a 1.5 mm thick slab heating to 150° C. for 15 minutes such that the reactants react and cure to form slabs. The slabs are then removed from the mold and placed in a 120° C. oven for 4 hours to complete the cure.

Samples of the slabs are evaluated to determine elongation and compression modulus, i.e., to evaluate brittleness. These samples are prepared by using a standard die cut method to a sample form of a standard tensile bar or 8 mm (diam) disc.

To determine compression modulus, compression modulus discs are aged in foil pans and tested via the method set forth below. Aging is accomplished at 225° C. as described above. Compression modulus testing is performed using a TA.XT2i Texture Analyzer (Stable Micro Systems) equipped with a 1-kg capacity, 0.1-g force resolution, load cell and aligned 10 mm diameter flat cylindrical test fixtures to compress the samples. The samples are 8 mm discs die cut from 1.5 mm thick hot pressed test slabs that were tested following aging by placing the aged disc adhered to the foil pans on the center of the lower stationary probe.

A compression strain from 0-50% is applied to the samples at a test speed of 0.1 mm/s. The strain is determined from the probe travel distance, d, and the sample thickness, h, as shown in equation 1: $\in(\%) = d/h \times 100$ (1)

Compressive moduli, $E_c$, of the elastomer discs are calculated from the slope of the compressive stress (compressive force divided by sample cross-sectional area) vs applied strain experimental data over the strain range of 15-35% where the samples exhibit uniform behavior.

In the Examples and throughout this disclosure, the terminology "$Fe^{Me}$" describes tris((1,1,1,3,5,5,5-heptamethyltrisiloxan-3-yl)oxy)iron. Similarly, the terminology "$Fe^{MePh}$" describes tris((1,3,5-trimethyl-1,1,5,5-tetraphenyltrisiloxan-3-yl)oxy)iron.

PDMS Test Matrix:

More specifically, elongation and compression modulus testing results of the examples that utilize the PDMS test matrix are set forth in the Tables below:

| Elongation Testing (% Elongation to Break) Ageing Time 225° C. in air (Days) | | | | | | | |
|---|---|---|---|---|---|---|---|
| Ageing Time (Days) | 0 | 1 | 2 | 5 | 10 | 20 | 30 |
| Comparative Example 1 | 387 | 362 | 133 | 61 | 34 | 15 | 7 |
| Example 1 ($Fe^{Me}$) | 361 | 274 | 114 | 122 | 130 | 98 | 82 |

Comparative Example 1 includes no additive.

Example 1 includes 250 ppm of iron delivered in/as $Fe(OSiMe(OSiMe_3)_2)_3$ as the additive.

The data set forth above demonstrates that adding a iron silyloxy stabilizer to the dimethylsilicone matrix is very effective at resisting hardening on exposure to high temperatures (as measured by % elongation to break) which is important for stable performance in devices. 50-1000 ppm of the additive in the matrix is suitable to obtain a significant benefit.

The compression modulus testing results of the PDMS matrix samples is set forth in the Tables below:

| Compression Modulus Testing (MPa) Ageing Time 225° C. in air (Days) | | | | | | | |
|---|---|---|---|---|---|---|---|
| Ageing Time (Days) | 0 | 0.333 | 1 | 2 | 3 | 5 | 7 |
| Comparative Example 1 | 2.42 | 2.35 | 1.11 | N/A | 10.35 | N/A | 16.94 |
| Example 2 5 ppm Iron Delivered In/As $Fe^{Me}$ | 2.64 | N/A | 2.69 | 2.75 | N/A | 2.18 | 2.37 |
| Example 3 50 ppm Iron Delivered In/As $Fe^{Me}$ | 2.66 | N/A | 2.14 | 2.56 | N/A | 2.13 | 2.34 |
| Example 1 250 ppm Iron Delivered In/As $Fe^{Me}$ | 2.76 | N/A | 2.34 | 1.97 | N/A | 1.93 | 2.06 |
| Example 4 750 ppm Iron Delivered In/As $Fe^{Me}$ | 2.77 | N/A | 2.06 | 2.01 | N/A | 2.06 | 1.87 |
| Example 5 2000 ppm Iron Delivered In/As $Fe^{Me}$ | 2.19 | N/A | 1.48 | 1.60 | N/A | 1.30 | 1.48 |
| Ageing Time (Days) | 9 | 10 | 14 | 20 | 26 | 30 | |
| Comparative Example 1 | N/A | N/A | 24.19 | N/A | N/A | N/A | |
| Example 2 5 ppm Iron Delivered In/As $Fe^{Me}$ | 2.23 | N/A | 1.99 | 2.21 | 2.04 | 2.08 | |
| Example 3 50 ppm Iron Delivered In/As $Fe^{Me}$ | 2.07 | N/A | 2.11 | 2.07 | 1.84 | 1.91 | |
| Example 1 250 ppm Iron Delivered In/As $Fe^{Me}$ | 2.18 | N/A | 2.21 | 2.70 | 2.77 | 2.71 | |
| Example 4 750 ppm Iron Delivered In/As $Fe^{Me}$ | 1.92 | N/A | 2.20 | 2.45 | 1.90 | 2.70 | |

| Compression Modulus Testing (MPa) Ageing Time 225° C. in air (Days) | | | | | |
|---|---|---|---|---|---|
| Example 5 2000 ppm Iron Delivered In/As Fe$^{Me}$ | 1.40 | N/A | 1.76 | 2.26 | 1.73 | 1.96 |

Comparative Example 1 includes no additive.

Example 1 is as described above.

Example 2 includes 5 ppm of iron delivered in/as Fe(OSiMe(OSiMe$_3$)$_2$)$_3$ as the additive.

Example 3 includes 50 ppm of iron delivered in/as Fe(OSiMe(OSiMe$_3$)$_2$)$_3$ as the additive.

Example 4 includes 750 ppm of iron delivered in/as Fe(OSiMe(OSiMe$_3$)$_2$)$_3$ as the additive.

Example 5 includes 750 ppm of iron delivered in/as Fe(OSiMe(OSiMe$_3$)$_2$)$_3$ as the additive.

The data set forth above demonstrates that adding a iron silyloxy stabilizer to the dimethylsilicone matrix is very effective at resisting hardening on exposure to high temperatures (as measured by modulus) which is important for stable performance in devices. 50-1000 ppm iron delivered in/as the additive in the matrix is suitable to obtain a significant benefit.

Phenyl Test Matrix:

The elongation and compression testing results of the phenyl matrix samples are set forth in the Tables below:

| Elongation Testing (% Elongation to Break) Ageing Time 225° C. in air (Days) | | | | | | | | | | | | | |
|---|---|---|---|---|---|---|---|---|---|---|---|---|---|
| Ageing Time (Days) | 0 | 0.33 | 1 | 2 | 3 | 5 | 7 | 9 | 10 | 14 | 20 | 26 | 30 |
| Comparative Example 2 | 68 | 59 | 33 | N/A | 8 | N/A | 3 | N/A | 2 | 3 | 4 | N/A | 4 |
| Example 6 (Fe$^{Meph}$) | 50 | N/A | 62 | 42 | N/A | 23 | 21 | 8 | N/A | 3 | 3 | 2 | 2 |

Comparative Example 2 includes no additive.

Example 6 includes 250 ppm of iron delivered in/as Fe(OSiMe(OSiPh$_2$Me)$_2$)$_3$ as the additive.

The data set forth above demonstrates that adding a iron silyloxy stabilizer to the methylphenylsilicone matrix is very effective at resisting hardening on exposure to high temperatures (as measured by % elongation to break) which is important for stable performance in devices. 50-1000 ppm of iron delivered in/as the additive in the matrix is suitable to obtain a significant benefit maintaining over 20% elongation for over twice as long of high temperature aging than the comparative (control) example.

The compression modulus testing results of the phenyl matrix samples is set forth in the Tables below:

| Compression Modulus Testing (MPa) Ageing Time 225° C. in air (Days) | | | | | | | |
|---|---|---|---|---|---|---|---|
| Ageing Time (Days) | 0 | 0.333 | 1 | 2 | 3 | 5 | 7 |
| Comparative Example 2 | 6.16 | 3.61 | 3.82 | N/A | 6.01 | N/A | 17.59 |
| Example 7 5 ppm Iron Delivered In/As Fe$^{Meph}$ | 6.68 | N/A | 4.39 | 5.13 | N/A | 3.91 | 5.93 |
| Example 8 50 ppm Iron Delivered In/As Fe$^{Meph}$ | 4.80 | N/A | 2.40 | 3.01 | N/A | 3.59 | 4.52 |
| Example 6 250 ppm Iron Delivered In/As Fe$^{Meph}$ | 4.38 | N/A | 4.43 | 4.51 | N/A | 5.31 | 6.07 |
| Example 9 750 ppm Iron Delivered In/As Fe$^{Meph}$ | 4.46 | N/A | 3.03 | 5.04 | N/A | 3.97 | 5.76 |
| Example 10 2000 ppm Iron Delivered In/As Fe$^{Meph}$ | 3.83 | N/A | 3.99 | 3.01 | N/A | 4.98 | 5.34 |
| Ageing Time (Days) | 9 | 10 | 14 | 20 | 26 | 30 | |
| Comparative Example 2 | N/A | 28.04 | 40.21 | 36.90 | N/A | 34.54 | |
| Example 7 5 ppm Iron Delivered In/As Fe$^{Meph}$ | 6.44 | N/A | 6.09 | 13.44 | 18.78 | 17.39 | |
| Example 8 50 ppm Iron Delivered In/As Fe$^{Meph}$ | 5.12 | N/A | 3.05 | 4.66 | 5.92 | 21.49 | |
| Example 6 250 ppm Iron Delivered In/As Fe$^{Meph}$ | 6.58 | N/A | 7.49 | 16.79 | 19.42 | 21.34 | |
| Example 9 750 ppm Iron Delivered In/As Fe$^{Meph}$ | 7.02 | N/A | 11.22 | 10.66 | 7.06 | 13.63 | |
| Example 10 2000 ppm Iron Delivered In/As Fe$^{Meph}$ | 5.11 | N/A | 8.26 | 9.27 | 11.35 | 6.72 | |

Comparative Example 2 includes no additive.

Example 6 is as described above.

Example 7 includes 5 ppm of iron delivered in/as Fe(OSiMe(OSiPh$_2$Me)$_2$)$_3$ as the additive.

Example 8 includes 50 ppm of iron delivered in/as Fe(OSiMe(OSiPh$_2$Me)$_2$)$_3$ as the additive.

Example 9 includes 750 ppm of iron delivered in/as Fe(OSiMe(OSiPh$_2$Me)$_2$)$_3$ as the additive.

Example 10 includes 2000 ppm of iron delivered in/as Fe(OSiMe(OSiPh$_2$Me)$_2$)$_3$ as the additive.

The data set forth above demonstrates that adding a iron silyloxy stabilizer to the methylphenylsilicone matrix is very effective at resisting hardening on exposure to high temperatures (as measured by modulus) which is important for stable performance in devices. 50-1000 ppm of iron delivered in/as the additive in the matrix is suitable to obtain a significant benefit.

Thermogravimetric Analysis:

Samples of the aforementioned PDMS and Phenyl Test Matrices with the respective additives described above are also evaluated via thermogravimetric analysis. Thermogravimetric analysis is accomplished by placing two 1 mm$^3$ cubes in a platinum TGA pan. The samples are placed in a N$_2$ atmosphere and heated via ramping of temperature from room temperature to 250° C. at 10° C./min and held at 250° C. for 1 hour to devolatilize the samples. The atmosphere is then switched to atmospheric air and the sample is ramped to 275° C. at 10° C./min and held for 3 hours.

Initial devolitalization (the weight % of the total sample lost during the initial 85 minute devolitalization step) is tabulated in the first column. The actual efficacy of the additive is measured by obtaining the slope (% weight loss/min) or weighted average of slopes for each matrix over a range of Fe concentrations.

|  | Devolitalization | Slope (% weight loss/min) |
|---|---|---|
| Comparative Example 1 | 1.955% | −0.066110 |
| Example 2<br>5 ppm Iron Delivered In/As Fe$^{Me}$ | 1.538% | −0.044224 |
| Example 3<br>50 ppm Iron Delivered In/As Fe$^{Me}$ | 1.518% | −0.006937 |
| Example 1<br>250 ppm Iron Delivered In/As Fe$^{Me}$ | 1.842% | −0.006730 |
| Example 4<br>750 ppm Iron Delivered In/As Fe$^{Me}$ | 2.150% | −0.006479 |
| Example 5<br>2000 ppm Iron Delivered In/As Fe$^{Me}$ | 2.893% | −0.007306 |

It can be determined from this testing that the FeMe modified PDMS matrix is effectively stabilized with as low as 5 ppm of Fe delivered in/as the additive. However, in various embodiments, the 250 ppm concentration may be utilized to balance Devolitalization and rate of degradation.

|  | Devolitalization | Slope |
|---|---|---|
| Comparative Example 2 | 0.402% | −0.017030% |
| Example 7<br>5 ppm Iron Delivered In/As Fe$^{MePh}$ | 0.485% | −0.014075% |
| Example 8<br>50 ppm Iron Delivered In/As Fe$^{MePh}$ | 0.781% | −0.010505% |
| Example 6<br>250 ppm Iron Delivered In/As Fe$^{MePh}$ | 1.419% | −0.009934% |
| Example 9<br>750 ppm Iron Delivered In/As Fe$^{MePh}$ | 1.351% | −0.010112% |
| Example 10<br>2000 ppm Iron Delivered In/As Fe$^{MePh}$ | 3.090% | −0.014640% |

In the PMPS matrix the same trend is observed although the initial volatilization is directly proportional to the amount of additive required to achieve the desired loading of Fe. Again, the 250 ppm concentration may be utilized to balance Devolitalization and rate of degradation.

Inductively Coupled Plasma-Optical Emission Spectrometer (ICP-OES) Analysis:

ICP-OES analysis is also performed. More specifically, additives Fe$^{Me}$ (Fe(OSiMe(OSiMe$_3$)$_2$)$_3$ and Fe$^{MePh}$ (Fe(OSiMe(OSiPh$_2$Me)$_2$)$_3$) are evaluated to determine theoretical amounts of Fe and actual amounts of Fe. Typically, all data is adjusted for instrument drift and matrix differences with the 1 ppm Sc internal standard. This adjustment is generally +/−0-5%. More specifically, ~0.05 grams of sample is weighed into a platinum dish. The samples are charred using H$_2$SO$_4$, taken to dryness then placed in a furnace to remove any residual carbon. The samples are then digested using H$_2$SO$_4$, HNO$_3$, and HF. The samples are taken to near dryness, then, brought to a final volume of 20 ml using ~5% HNO$_3$. A 2nd 15× dilution into 5% HNO$_3$ is performed prior to analysis. 1 ppm of Sc is added as an internal standard. The samples are then analyzed via Inductively Coupled Plasma-Optical Emission Spectrometer (ICP-OES).

| Compound | Theoretical % Fe | Actual % Fe |
|---|---|---|
| Structure I: Fe$^{Me}$<br>Fe(OSiMe(OSiMe$_3$)$_2$)$_3$ | 7.27 | 7.11 |
| Structure II: Fe$^{MePh}$<br>Fe(OSiMe(OSiPh$_2$Me)$_2$)$_3$ | 3.69 | 2.92 |

The aforementioned data show that analysis of the Fe content of the aforementioned compounds enables refined targeting of final metal content in an article or composition. The molecular complexity of Fe and the variety of possible synthetic methods leading to the additives allow for variance of the final metal content.

Figure 2:
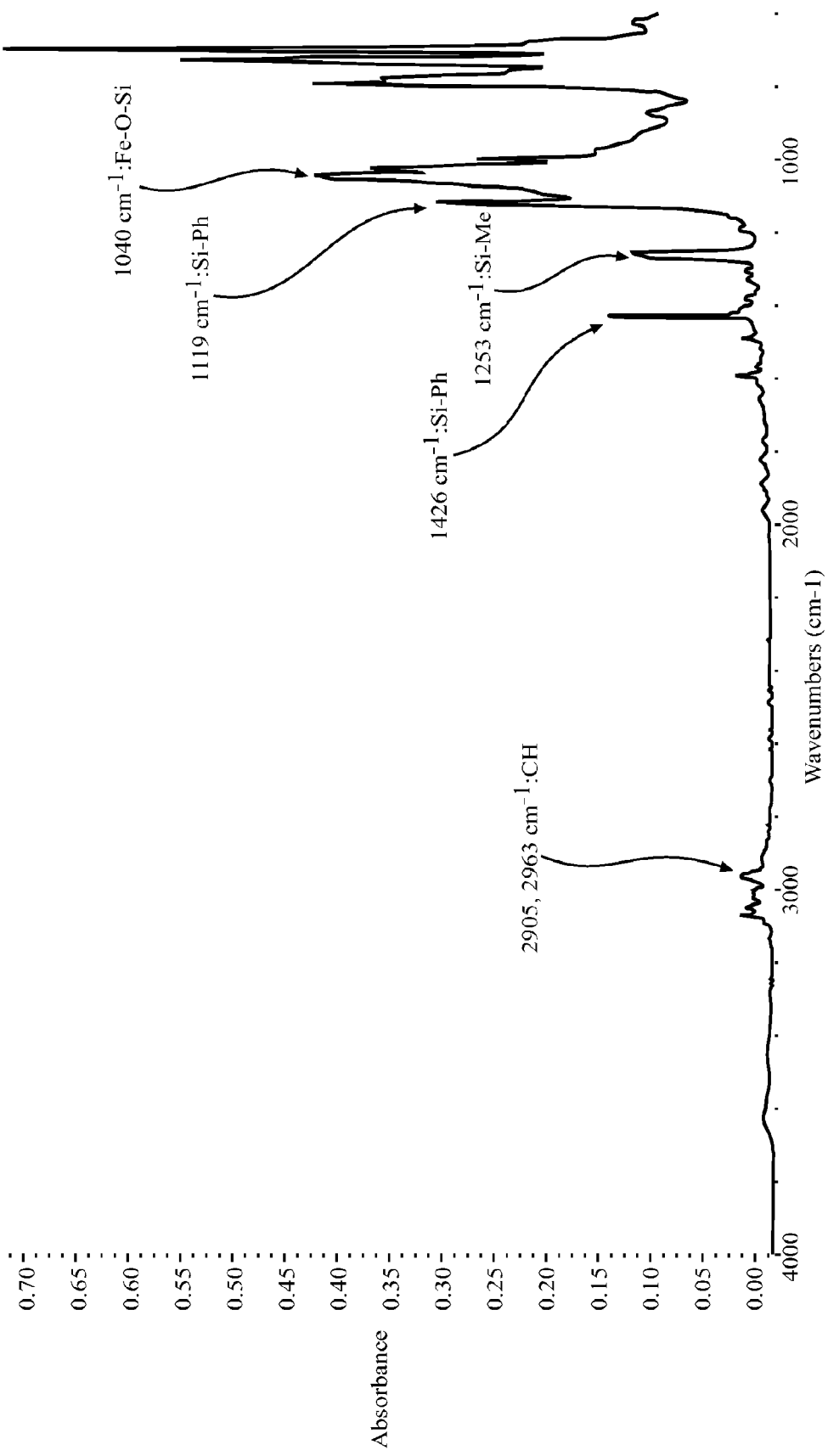
FIG. 2 is an ATR-FTIR spectrograph of Fe$^{MePH}$, (Fe(OSiMe(OSiPh$_2$Me)$_2$)$_3$).

ATR-FTIR Spectroscopy:

ATR-FTIR Spectrographs are also generated for Fe$^{Me}$ (Fe(OSiMe(OSiMe$_3$)$_2$)$_3$ and Fe$^{MePh}$ (Fe(OSiMe(OSiPh$_2$Me)$_2$)$_3$) and are set forth as FIGS. 1 and 2, respectively. More specifically, ATR-FTIR spectra are acquired using a Nicolet 6700 FTIR with a ZnSe crystal, DTGS TEC detector, KBr beamsplitter, and IR source in the range of 400 to 4000 cm$^{-1}$. The sample spectra (32 scans) are collected as neat materials in direct contact with the crystal. These spectrographs show iron-oxygen-silicon bonds present in the compounds, shown as various peaks, as understood by one of skill in the art.

In various non-limiting embodiments, this disclosure includes one or more compounds, method steps, devices, or analytical steps, or any other description, as set forth in the simultaneously filed U.S. Provisional patent application Ser. No. 61/873,160, which is expressly incorporated herein in its entirety relative to these non-limiting embodiments.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

What is claimed is:

1. An additive for a silicone encapsulant, said additive having the structure:

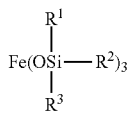

wherein $R^1$ and $R^2$ are each $-O-Si(R^4)(R^5)(R^6)$ and each of $R^4$, $R^5$, and $R^6$ is independently chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups, and wherein $R^3$ is independently chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups.

2. The additive of claim 1 wherein at least 20 mol percent of a total of the groups $R^3$-$R^6$ are methyl groups.

3. The additive of claim 1 wherein at least 20 mol percent of a total of the groups $R^3$-$R^6$ are phenyl groups.

4. The additive of claim 1 wherein each $R^3$, $R^4$, and $R^6$ is a methyl group.

5. The additive of claim 1 wherein each $R^3$, $R^4$, and $R^6$ is a phenyl group.

6. The additive of claim 1 that is further defined as having the structure:

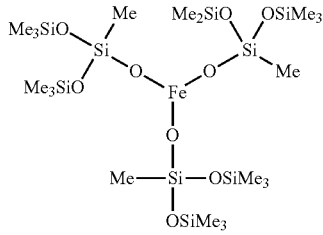

wherein Me is methyl.

7. The additive of claim 1 that is further defined as having the structure:

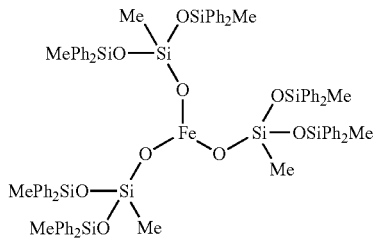

wherein Me is methyl and Ph is phenyl.

8. The additive of claim 1 that is further defined as:
a reaction product of a reaction of an iron alkoxide and a hydroxyl functional organosiloxane; or
a reaction product of a reaction of iron metal and a hydroxyl functional organosiloxane.

9. The additive of claim 8 wherein the hydroxyl functional organosiloxane has the formula $M^1D^{R,OH}M^2$, wherein R is chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups.

10. The additive of claim 8 wherein the hydroxyl functional organosiloxane has the structure:

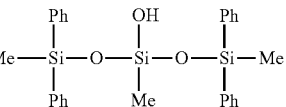

wherein Me is methyl and Ph is phenyl.

11. A iron silyloxide cluster comprising 2 to 10 units of the additive of claim 1.

12. A silicone encapsulant comprising said additive of claim 1 and a silicone.

13. A silicone encapsulant comprising:
A. an additive having the structure:

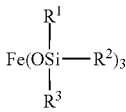

wherein $R^1$ and $R^2$ are each $-O-Si(R^4)(R^5)(R^6)$ and each of $R^4$, $R^5$, and $R^6$ is independently chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups, and wherein $R^3$ is independently chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups; and
B. a polyorganosiloxane.

14. A device comprising an electronic component and said encapsulant of claim 13.

15. A method of making an additive having the structure:

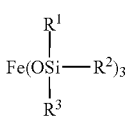

wherein $R^1$ and $R^2$ are each $-O-Si(R^4)(R^5)(R^6)$ and each of $R^4$, $R^5$, and $R^6$ is independently chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups, and wherein $R^3$ is independently chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups,
wherein the method comprises the step of reacting iron metal or an iron (III) compound with a hydroxyl functional organosiloxane.

* * * * *